(12) United States Patent
Goris et al.

(10) Patent No.: US 10,967,074 B2
(45) Date of Patent: *Apr. 6, 2021

(54) EYE DROP COMPOSITION

(71) Applicant: ARATANA THERAPEUTICS NV, Heverlee (BE)

(72) Inventors: Nesya Goris, Kessel-Lo (BE); Johan Neyts, Kessel-Lo (BE); Erwin Blomsma, Linden (BE); Stefaan Wera, Bierbeek (BE); Ainola Billiet, Bierbeek (BE); Joeri Auwerx, Bierbeek (BE); Veerle Debeurme, Kessel-Lo (BE); Maryline Roe, Toulouse (FR); Pascal Puig, Cazilhac (FR)

(73) Assignee: ARATANA THERAPEUTICS, INC., Leawood, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,365

(22) Filed: Aug. 17, 2015

(65) Prior Publication Data

US 2015/0352118 A1 Dec. 10, 2015

Related U.S. Application Data

(63) Continuation of application No. 14/373,322, filed as application No. PCT/EP2012/050843 on Jan. 20, 2012, now Pat. No. 9,107,943.

(51) Int. Cl.
| | |
|---|---|
| *A61K 49/00* | (2006.01) |
| *A61K 31/305* | (2006.01) |
| *A61K 47/40* | (2006.01) |
| *A61K 31/522* | (2006.01) |
| *A61K 9/00* | (2006.01) |
| *A61K 47/24* | (2006.01) |

(52) U.S. Cl.
CPC ........ *A61K 49/0004* (2013.01); *A61K 9/0048* (2013.01); *A61K 31/305* (2013.01); *A61K 31/522* (2013.01); *A61K 47/24* (2013.01); *A61K 47/40* (2013.01)

(58) Field of Classification Search
CPC .............. A61K 49/0004; A61K 9/0048; A61K 31/305; A61K 47/24; A61K 47/40; A61K 31/522; A61K 9/08; A61P 31/22; A61P 27/02

See application file for complete search history.

(56) References Cited

U.S. PATENT DOCUMENTS

| 9,040,699 B2 | 2/2015 | Kiss et al. |
| 9,107,943 B2 | 4/2015 | Goris et al. |

FOREIGN PATENT DOCUMENTS

| CN | 101433721 | 5/2009 |
|---|---|---|
| EA | 2001/00316 | 2/2002 |
| EP | 0502690 | 9/1992 |
| EP | 0649840 | 4/1995 |
| EP | 0675123 | 10/1995 |
| EP | 0890574 | 1/1999 |
| JP | H0578357 | 3/1993 |
| JP | H0680670 | 3/1994 |
| JP | H0841035 | 2/1996 |
| JP | 2004-026695 | 1/2004 |
| RU | 2414898 | 3/2011 |
| WO | WO 2002/005822 | 1/2002 |
| WO | WO 2010/042030 | 4/2010 |
| WO | WO 2013/107515 A1 | 7/2013 |

OTHER PUBLICATIONS

International Search Report of International Patent Application PCT/EP2012/050843, provided by the International Search Authority, dated Sep. 4, 2012, 3 pages.

Itahashi et al., "A-5021: a new acyclovir analogue inhibits murine herpetic keratitis", Cornea, 2008, 27(3):334-338 (Abstract).

Iwayama et al., "Antiherpesvirus Activities of (1'S,2'R)-9-{[1',2'-Bis(hydroxymethyl)cycloprop-1'-yl]methyl}guanine (A-5021) in Cell Culture", Antimicrobial Agents and Chemotherapy, 1998, 42(7):1666-1670.

Loftsson et al., "Effect of Cyclodextrins on Topical Drug Delivery to the Eye", Drug Development and Industrial Pharmacy, 1997, 23(5):473-481.

Loftssona et al., "Cyclodextrins in Ophthalmic Drug Delivery", Advanced Drug Delivery Reviews, 1999, 36(1):59-79 (Abstract).

Neyts et al., "Anti-herpesvirus activity of (1'S,2'R)-9-[[1',2'-bis(hydroxymethyl)-cycloprop-1'-yl]methyl]guanine (A-5021) in vitro and in vivo", Antiviral Research, 2001, 49(2):115-120 (Abstract).

Chen et al., "An Improved Synthesis of 9-[2-(Diethoxyphosphonomethoxy) Ethyl]Adenine and its Analogs with Other Purine Bases Utilizing the Mitsunobu Reaction," Nucleosides & Nucleotides, 15(11&12): 1771-1778 (1996).

CN101433721, Univ Huazhong Science Tech, "Nimesulide-hydroxypropyl-beta-cyclodextrin inclusion compound eye drops and preparation method thereof," May 20, 2009, English language machine translation of abstract, Espacenet, date obtained: Jun. 14, 2017, 1 page, <URL: https://worldwide.espacenet.com/publicationDetails/biblio?II=0&ND=3&adjacent=true&locale=en_EP&FT=D&date=20090520&CC=CN&NR=101433721A&KC=A>.

Csuk et al., "Synthesis of spacered cyclopropyl nucleoside analogues as potential antiviral agents," Tetrahedron, 55(28): 8409-8422 (1999).

(Continued)

*Primary Examiner* — Robert S Cabral
(74) *Attorney, Agent, or Firm* — Hoxie & Associates LLC

(57) ABSTRACT

The present invention relates to an eye-drop composition comprising 2-amino-9-[[(1S,2R)-1,2-bis(hydroxymethyl) cyclopropyl]methyl]-1,9-dihydro-6H-Purin-6-one, and the use thereof for the diagnosis and treatment of herpetic eye infections in companion animals.

15 Claims, No Drawings

(56) References Cited

OTHER PUBLICATIONS

EA200100316, Les Laboratoires Servier, "Method for Preparing a Solution for Nasal Spray Containing Sex Hormones and a Cyclodextrin," Feb. 28, 2002, English language machine translation of abstract, Espacenet, date obtained: Jun. 14, 2017, 2 pages, <URL: https://worldwide.espacenet.com/publicationDetails/biblio?CC=EA&NR=200100316A1&KC=A1&FT=D&ND=3&date=20020228&DB=&locale=en_EP>.

Gallos et al., "Carbocyclic Nucleoside Precursors by Intramolecular Cyclopropanation of Sugar-Derived Diazo Compounds," Tetrahedron Letters, 42: 7489-7491 (2001).

Gianni et al., "The Role of the Generalized Anomeric Effect in the Conformational Analysis of 1,3-dioxacycloalkanes. Conformational Analysis of 3,5-thoxabicyclo[5.1.0]octanes and 3,5,8-trioxabicyclo[5.1.0]octanes," J. Org. Chem., 42(2): 365-368 (1977).

JPH0578357, Ajinomoto Co., Ltd., "New Cyclopropane Derivative, Its Production and Antiviral Agent Composition Containing the Same," Mar. 30, 1993, English language machine translation of abstract, Espacenet, date obtained: Jun. 14, 2017, 2 pages, <URL: https://worldwide.espacenet.com/publicationDetails/biblio?II=0&ND=3&adjacent=true&locale=en_EP&FT=D&date=19930330&CC=JP&NR=H0578357A&KC=A>.

JPH0680670, Ajinomoto Co., Ltd., "Cyclopropane Derivative and its Production," Mar. 22, 1994, English language machine translation of abstract, Espacenet, date obtained: Jun. 14, 2017, 2 pages, <URL: https://worldwide.espacenet.com/publicationDetails/biblio?II=0&ND=3&adjacent=true&locale=en_EP&FT=D&date=19940322&CC=JP&NR=H0680670A&KC=A>.

JPH0841035, Ajinomoto Co., Ltd., "Cyclopropane Derivative and its Production," Feb. 13, 1996, English language machine translation of abstract, Espacenet, date obtained: Jun. 14, 2017, 2 pages, <URL: https://worldwide.espacenet.com/publicationDetails/biblio?II=0&ND=3&adjacent=true&locale=en_EP&FT=D&date=19960213&CC=JP&NR=H0841035A&KC=A>.

Khlebnikova et al., "Synthesis of New Chiral Phosphorous- and Nitrogen-Containing Ligands from Resin Acids," Chirality, 16: S40-50 (2004).

Kumara Swamy et al., "Mitsunobu and Related Reactions: Advances and Applications," Chem. Rev, 109: 2551-2651 (2009).

Onishi et al., "Synthesis and Antiviral Activity of Novel Anti-VZV 5-Substituted Uracil Nucleosides with a Cyclopropane Sugar Moiety," J. Med. Chem., 43: 278-282 (2000).

Park et al., "Synthesis of Enantiomerically Pure D- and L-bicyclo[3.1.0]hexenyl carbanucleosides and Their Antiviral Evaluation," Bioorganic & Medicinal Chemistry, 19: 3945-3955 (2011).

RU2414898, Valenta Farmatsevtika Aoot, "Pharmaceutical Composition in Form of Solution for Injections, Which has Nootropic Activity, and Method of its Obtaining," Mar. 27, 2011, English language machine translation of abstract, Espacenet, date obtained: Jun. 14, 2017, 1 page, <URL: https://worldwide.espacenet.com/publicationDetails/biblio?II=0&ND=3&adjacent=true&locale=en_EP&FT=D&date=20110327&CC=RU&NR=2414898C1&KC=C1>.

Sekiyama et al., "Synthesis and Antiviral Activity of Novel Acyclic Nucleosides: Discovery of a Cyclopropyl Nucleoside with Potent Inhibitory Activity against Herpesviruses," J. Med. Chem., 41: 1284-1298 (1998).

EYE DROP COMPOSITION

This application is a continuation application of U.S. application Ser. No. 14/373,322 filed Jul. 18, 2014, which application is a 35 U.S.C. § 371 National Phase Application of International Application No. PCT/EP2012/050843, filed Jan. 20, 2012 the contents of each of which are incorporated herein by reference.

FIELD OF THE INVENTION

The present invention relates to an eye-drop composition, and the use thereof for the diagnosis and treatment of eye infections in animals.

BACKGROUND OF THE INVENTION

The diagnosis of ocular infections in animals can be problematic. For example, the diagnosis of feline herpes virus 1 (FHV-1) is typically based on clinical signs and PCR-confirmed presence of viral DNA. However, diagnosis is complicated by the occurrence of false negative PCR results and the fact that a positive PCR result may also reflect low level viral shedding or even latent infection. Therefore, it is often impossible to prove that the observed clinical signs are indeed linked to the presence of FHV-1 DNA. An accurate and quick diagnosis is key to ensure an efficient treatment and to avoid over-medication.

Different antiviral compounds are known for the treatment of herpes virus infections. The compound 2-amino-9-[[(1S,2R)-1,2-bis(hydroxymethyl)cyclopropyl]methyl]-1,9-dihydro-6H-Purin-6-one (also known as "A-5021") is a potent inhibitor of herpes virus replication (Neyts et al., Antiviral Research 2001, 49, 115-120; Iwayama et al., Antimicr. Agents Chemother. 1998, 42, 1666-1670). For example, A-5021 has been reported to be a potent and selective antiviral agent against herpes simplex virus type 1 (HSV-1), herpes simplex virus type 2 (HSV-2) and varicella-zoster (VZV) in vivo. However, the medical and veterinary use of A-5021 is hampered by its poor solubility. Solubilization of A-5021 to pharmacologically active concentrations is heavily pH dependent, and obtaining a stable solution comprising more than 1 mg/mL of A-5021 (or 0.1% w/v A-5021 solutions) typically requires pH values of either below 4 or above 10. Eye drop compositions having a pH value of about 7 and comprising more than 1 mg/mL A-5021 have been reported by Itahashi et al. (Cornea 2008, 27, 334-338), but these compositions have a poor stability and thus can not be used in practice. Therefore the preparation of stable pharmaceutical formulations of solubilized A-5021 is not straightforward.

There is a need for improved methods of diagnosing viral infections and for compositions which effectively treat (ocular) herpetic infections, which mitigate at least one of the problems stated above.

SUMMARY OF THE INVENTION

The present invention describes a method for solubilizing A-5021 under isotonic and pH neutral conditions in concentrations between 1-10 mg/mL (0.1-1% w/v), allowing the use of A-5021 in stable liquid formulations such as eye-drops. Such eye drops are particularly useful in the treatment and diagnosis of ocular infections in animals In a first aspect, the present invention provides compositions comprising A-5021 at a concentration of at least 0.1% w/v which are stable. More particularly, the compositions are stable in that the A-5021 does not precipitate, more particularly no precipitation is observed within 1-48 hrs, preferably within 1 week, more preferably within 1 month and most preferably within 3 months or longer after making of the composition. More particularly, the compositions of the invention comprise:
at least 0.1% w/v A-5021; and
at least 10% w/v of a cyclodextrin.

In particular embodiments, the composition is an aqueous solution. In certain embodiments, the composition is an ophthalmic solution. In particular embodiments, the cyclodextrin used in the compositions of the invention is hydroxypropyl beta-cyclodextrin. In certain embodiments, the composition further comprises at least 0.008% w/v thiomersal.

In a further aspect, the present invention provides compositions as described above, for use as a diagnostic and/or a therapeutic composition.

In certain embodiments, the compositions are for use in a method for the treatment of an ocular herpetic infection. In particular embodiments, the ocular infection to be treated is an ocular infection of a companion animal. In certain embodiments, said companion animal is a feline. In particular embodiments, the ocular infection to be treated using the compositions of the present invention is an ocular infection of a feline. In particular embodiments, the treatment methods envisaged comprise applying the composition of the invention onto the eye two or three times per day for at least seven days.

In certain embodiments, said the compositions of the present invention are envisaged for use in a method of diagnosis of an ocular herpetic infection. In particular embodiments, the ocular infection is an ocular infection in a companion animal. In particular embodiments, the companion animal is a feline. In particular embodiments, said the methods of diagnosis envisaged comprise applying the composition of the invention onto the eye two or three times per day for one to seven days and determining whether or not the clinical symptoms of the eye infection have decreased, whereby a decrease in clinical symptoms is indicative of the fact that the ocular infection is an ocular herpetic infection.

In a further aspect, the present invention provides methods for preparing stable ophthalmic solutions comprising A-5021. More particularly, the methods comprise the steps of:
a) providing a solution comprising at least 10% w/v of a cyclodextrin;
b) adding A-5021 to said solution;
c) solubilizing the A-5021 added in step b);
d) repeating steps b) and c) until a concentration of A-5021 in said solution of at least 1 mg/mL is obtained;
e) optionally, adding at least 0.08 mg/mL thiomersal.

In particular embodiments, said cyclodextrin in step a) is hydroxypropyl beta-cyclodextrin.

DETAILED DESCRIPTION OF THE INVENTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes"

or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

The term "w/v" as used herein refers to weight/volume. If it is stated that a solution comprises a certain compound in a concentration of x % w/v, this means that 1 L of that solution comprises 10 g of that compound.

The term "sulfo", by itself or as part of another substituent, refers to a —SO$_3$H group or a salt thereof.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the features of the claimed embodiments can be used in any combination.

The present invention provides liquid compositions comprising the compound A-5021 (i.e. 2-amino-9-[[(1S,2R)-1,2-bis(hydroxymethyl)cyclopropyl]methyl]-1,9-dihydro-6H-Purin-6-one), which is represented by formula (I):

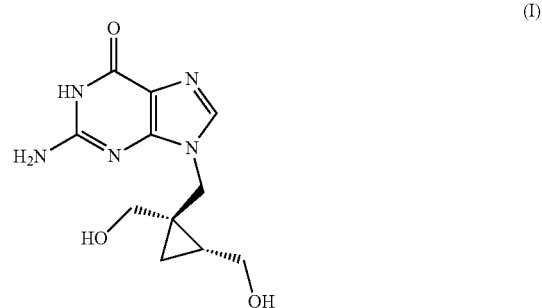 [SMILES: Nc1nc2c(ncn2C[C@]2(CO)C[C@H]2CO)c(=O)[nH]1]

Unlike other nucleoside analogues, the compound A-5021 is poorly soluble in water. While given the structural similarities between A-5021 and the known anti-herpes drug penciclovir (i.e. 2-amino-9-[4-hydroxy-3-(hydroxymethyl)butyl]-3H-purin-6-one) it appears likely that it can be formulated as a sodium salt hydrate formulation, such a formulation is highly alkaline and therefore not compatible with applications wherein a physiological composition is required.

Thus, particular applications of A-5021 have been hampered by the inability to obtain sufficiently high concentrations of the active ingredient in a physiologically compatible liquid composition.

For instance, a suitable eye-drop formulation should have a neutral pH (i.e. a pH of 7) or close to neutral pH. The present inventors have now found that only cyclodextrins such as hydroxypropyl beta-cyclodextrin (Kleptose® HPB) are suitable for physiological liquid formulations of A-5021, as only the use of such agents results in a 0.1% to 1% w/v solution which is well tolerated by healthy and herpes virus-infected eyes (see example a1). In addition, the formulation should be stable, allowing for repeated use with several hours interval, preferably for several days or weeks, without the formation of precipitation in the composition.

Accordingly, in a first aspect, the present invention provides compositions comprising:
at least 0.1% w/v A-5021; and
a cyclodextrin.

The provision of the active ingredient in concentrations of 0.1% w/v or more in a physiologically tolerated solution allows the formulation thereof in different forms such as aqueous solutions (which can be applied as sprays or drops), aqueous gels, etc.

In particular embodiments, the composition is an ophthalmic solution.

In particular embodiments, the composition further comprises one or more solvents, for example water. In certain embodiments, the composition is an aqueous solution. The term "aqueous" as used herein means that more than 50 percent by volume of the solvent is water.

In particular embodiments, the composition according to the present invention consists of a solvent, at least 0.1% w/v A-5021 and a cyclodextrin. In certain embodiments, the composition according to the present invention consists of at least 0.1% w/v A-5021 and a cyclodextrin.

The A-5021 concentration of 0.1% w/v ensures the minimal sufficient therapeutic effect of the composition for the treatment of herpes virus infections in companion animals or other animal species larger than rodents. However, in particular embodiments, a higher concentration of A-5021 may lead to an enhanced therapeutic effect of the composition. Accordingly, in certain embodiments, the composition comprises at least 0.10%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95% or 1% A-5021 (the percentages are % w/v).

The use of a cyclodextrin allows to obtain stable formulations comprising an A-5021 concentration of at least 0.1% w/v, for example 0.2% w/v or 0.5% w/v, which is well tolerated when used in applications which require physiologically tolerable solutions such as applications to the eye and/or wounds. A higher cyclodextrin concentration typically allows obtaining a higher concentration of A-5021. In particular embodiments, the composition comprises at least 10%, 15%, 20%, 25%, 30%, 35%, 40%, 45%, 50%, 55%, 60%, 65%, 70%, 75%, 80%, 85%, 90%, 95% or 99% cyclodextrin (the percentages are % w/v).

The cyclodextrin may comprise one or more of a beta-cyclodextrin, a gamma-cyclodextrin or an alpha-cyclodextrin. In certain embodiments, the cyclodextrin comprises a beta-cyclodextrin. In further embodiments, the cyclodextrin comprises a modified or substituted cyclodextrin. For example, the cyclodextrin may comprise one or more substituents selected from hydroxypropyl (e.g. 2-hydroxypropyl), sulfobutyl and methyl. In certain embodiments, the cyclodextrin is a hydroxypropyl (beta-)cyclodextrin (e.g. Kleptose® HPB), more particularly 2-hydroxypropyl (beta-)cyclodextrin. Hydroxypropyl beta-cyclodextrin significantly increases the solubility of A-5021, and is well tolerated when applied to the eye. In particular embodiments, the cyclodextrin comprises a methyl-cyclodextrin, for example a randomly methylated beta-cyclodextrin. In certain embodiments, the cyclodextrin is a sulfobutylether cyclodextrin, for example a sulfobutylether beta-cyclodextrin (e.g. Captisol®).

In particular embodiments, the compositions according to the present invention further comprise one or more preservatives. Indeed, multi-dose pharmaceutical formulations typically comprise preservatives to allow their use during multiple daily dosing and/or several days after opening of the packaging. However, such preservatives should not compromise the physiological tolerability of the composition while ensuring the stability of the composition over a prolonged period of time.

The inventors found that Thiomersal is most effective in preservative efficacy tests while not inducing adverse effects. Accordingly, in particular embodiments, the composition according to the present invention further comprises Thiomersal (i.e. sodium (2-carboxylatophenyl)sulfanyl-ethylmercury; also known as thimerosal), which is represented by the compound of formula (II):

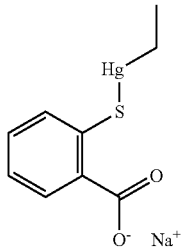

(II)

The inventors have found that a Thiomersal concentration of 0.005% w/v or more (e.g. 0.008%, 0.01% or 0.02% w/v) is particularly effective for antimicrobial preservation (see example a1). Accordingly, in particular embodiments, the composition according to the present invention comprises at least 0.005, 0.008, 0.01, 0.015 or 0.02% w/v Thiomersal. In particular embodiments, the composition comprises at least 0.01% w/v Thiomersal and at least 0.2% w/v A-5021. The maximum authorized concentration of Thiomersal is regulated in various countries. Therefore, the Thiomersal concentration is preferably not higher than 0.02% w/v, such as 0.01, 0.015, 0.018, or 0.02% w/v.

In order to allow the use of the compositions according to the present invention in applications requiring strict physiological tolerability, such as in ophthalmic applications, the pH of the composition should be within the ocular comfort range. Accordingly the pH of the compositions of the present invention preferably ranges between 5 and 8.5, particularly between 6 and 8, more particularly between 6.4 and 7.8, most particularly between 6.6 and 7.4. In particular embodiments, the compositions according to the present invention further may comprise one or more buffering agents, such as a phosphate buffer like sodium phosphate. In certain embodiments, the compositions according to the present invention may further comprise one or more pH adjusting agents, such as sodium hydroxide, hydrochloric acid or combinations thereof.

It has been found by the present inventors that the use of cyclodextrin does not require the use of solubilizing agents with an elevated pH.

Furthermore, the physiological tolerability of the compositions of the present invention implies a minimal discrepancy with local osmotic pressure. In particular embodiments, where the compositions are for ophthalmic use, the compositions preferably have a (nearly) tear-isotonic osmotic pressure or osmolarity (i.e. about 300 mOsm/L), preferably between 200 and 400 mOsm/L. In certain embodiments, the compositions according to the present invention may further comprise one or more tonicity adjusting agents, for example selected from the group consisting of dextrose, glycerin, mannitol, potassium chloride, sodium chloride and phosphate buffers. Tonicity adjusting agents can be used to modify the osmotic pressure or osmolarity of a composition.

The skilled person will further understand that the compositions of the present invention are preferably sterile and devoid of exogenous particles.

Thus, as indicated above, the compositions of the present invention may comprise, in addition to the active ingredient A-5021, and cyclodextrin, one or more preservatives and/or buffering agents. In particular embodiments, the compositions of the present invention consist essentially of the active ingredient and cyclodextrin, and an aqueous solution such as a buffer. In particular embodiments, the compositions do not comprise a solubilizing agent with an elevated pH.

The inventors have found that the compositions according to the present invention are particularly useful for the treatment and diagnosis of herpetic infections. Accordingly, in a further aspect, the present invention provides a composition as described herein above for use in medicine, more particularly for use as a therapeutic and/or a diagnostic composition.

In particular embodiments, the present invention provides a composition as described herein above for use in a method for the treatment of a herpetic infection. In certain embodiments, the herpetic infection is an ocular herpetic infection. Ocular herpes virus infections have been observed in various animals including cats (e.g. examples b1, b2 and b3 below), dogs (e.g. Ledbetter et al., Veterinary Microbiology 2009, 138, 98-105) and horses (e.g. Kershaw et al., Virus Research 2001, 80, 93-99). Accordingly, in particular embodiments, the infection is an infection in an animal, for example selected from a feline, a canine and an equine.

In particular embodiments, said the compositions are envisaged for the treatment of an infection in a companion animal, more particularly a feline and even more particularly a cat. Thus, in particular embodiments, the infection is a feline herpes virus infection. The present inventors have found that the compositions of the present invention very effectively treat ocular herpetic infections in companion animals such as felines, for example cats.

Moreover, the inventors have found that the treatment of herpetic eye infections using the compositions according to the present invention is particularly successful when the composition is applied onto the (affected) eye two or three times per day. The optimal application frequency may depend on factors such as the severity of the infection and the concentration of A-5021 in the composition. In particular embodiments, compositions comprising about 0.5% w/v A-5021 are applied two times per day. In certain embodiments, compositions with lower concentrations, for example about 0.2% w/v, are applied three times per day. In particular embodiments, the composition is applied onto the (affected) eye two or three times per day, for at least one, two, three or four weeks. In certain embodiments, the treatment is continued 1, 2, 3, 4, 5, 6, 7, 8, 9, 10 or more days after disappearance of the clinical symptoms.

The compositions according to the invention, for use in the treatment of ocular infections are typically applied directly to the eye, more particularly on the cornea. However, also other means of application are envisaged, such as intraocular injection.

Feline herpes virus is one of the most common infectious diseases in cats. Accordingly, the present invention provides therapeutic formulations for use in the treatment of eye infections of cats. In particular embodiments, the treatment regimen is as described above. Thus in particular embodiments the treatment regimen of a composition comprising 0.1 to 1% w/v A-5021, is two or three applications per day. Typically, ocular infections are characterized by one or more symptoms such as ocular discharge, conjunctivitis, keratitis, dendritic ulcers, geographic ulcers, corneal sequestrum, corneal edema, vascularization, blindness, eosinophilic conjunctivitis, eosinophilic keratitis, stromal keratitis, uveitis, and dry eye. The ocular symptoms are usually preceded by a history of respiratory signs.

Moreover, the present inventors have found that the compositions of the present invention are exceptionally well tolerated by animals suffering from clinical symptoms of ocular infections which increase sensitivity in the eye, such as the presence of ocular discharge, conjunctivitis, keratitis, dendritic ulcers, geographic ulcers, corneal sequestrum, corneal edema, vascularization, blindness, eosinophilic conjunctivitis, eosinophilic keratitis, stromal keratitis, uveitis, dry eye or other clinical symptoms. Thus, in particular embodiments the compositions of the present invention are for use in the treatment of ocular infections characterized by one or more of the symptoms described above.

In particular embodiments, the compositions of the present invention are used in the treatment of ocular infections which have been diagnosed to be herpes virus infections. For instance, dendritic and geographic ulcers (feline ulcerative keratitis) are considered a pathognomonic clinical manifestation of FHV-1. Thus, in particular embodiments, the compositions are used for the treatment of an ocular infection in a feline suffering from a dendritic or geographic ulcer.

Additionally, as described above, it is possible to determine the presence of a herpes infection virologically. Thus, in particular embodiments, the compositions are used for the treatment of an ocular infection in a feline which has been diagnosed as infected with a feline herpes virus 1 (FHV-1).

In accordance with the above, the present invention provides the use of compositions as described herein above for the manufacture of a medicament for the treatment of an ocular infection, more particularly an ocular herpetic infection, as described herein. Similarly, the present invention provides methods of treatment of an ocular infection, comprising the application of a composition as described herein above to the (infected) eye, more particularly two or three times per day, as described herein above.

It has been observed that the treatment of ocular herpes virus infections with the compositions according to the present inventions leads to significant improvement of the clinical symptoms within one week, and even after one or two days. In view of this surprising efficacy, the compositions according to the present invention are additionally suitable in methods of diagnosis of ocular infections, more particularly feline ocular infections. More particularly, the inventors have found that the compositions according to the present invention may be used as a diagnostic tool to confirm or exclude feline herpes virus 1 (FHV-1) as the cause of ocular infections in felines.

Indeed, ocular herpes virus infections typically result in a variety of different and often aspecific clinical manifestations among which are ocular discharge, conjunctivitis, keratitis, corneal sequestrum, eosinophilic conjunctivitis, eosinophilic keratitis, stromal keratitis, uveitis, and dry eye. In the case of feline ocular disease, other viral, bacterial and fungal pathogens may provoke similar clinical disease. More specifically, feline calicivirus, feline immunodeficiency virus, feline leukemia virus, *Chlamydophila felis*, *Mycoplasma* spp. (*M. felis* and *M. gatae*), and even immune mediated diseases have been described to be at origin of one or more of these clinical ocular manifestations.

Consequently, clinical diagnosis of FHV-1 is challenging and laboratory confirmation is often needed. However, most virological techniques for detecting FHV-1 are relatively insensitive and are often a source of false-negative and false-positive results. Polymerase chain reaction (PCR) currently is considered the most sensitive method of detecting FHV-1 DNA in ocular tissues. However, PCR test results seem inconsistent, leading many veterinary ophthalmologists to abandon PCR testing as a means of diagnosis, instead relying on clinical history and presentation alone.

Because A-5021 is a highly specific anti-herpes drug which is ineffective against bacterial and fungal infections and on viruses other than herpes viruses (such as FHV-1) that may cause similar symptoms (such as feline calicivirus, feline leukemia virus and feline immunodeficiency virus), a rapid response upon treatment with a composition according to the present invention allows its use as a diagnostic, more particularly as a diagnostic therapeuticum. Hence in case of eye infections in felines of unknown etiology, the response to treatment with a composition according to the present invention allows to make a first-line diagnosis of the ocular infection, more particularly makes it possible to diagnose the infections as herpetic or non-herpetic.

Accordingly, the present invention further provides compositions as described herein above, for use in a method of diagnosis of an ocular infection, more particularly in an ocular infection in a companion animal. More particularly, the methods of diagnosis envisaged in this context comprise the steps of a) administering the composition of the invention in a formulation and dosage as described above and b) determining within a specified period whether or not clinical symptoms have improved, whereby improvement of the clinical symptoms is an indication of the presence of a herpes virus infection. In further particular embodiments, the methods of the present invention comprise administering a composition according to the invention daily and determining within 1 to 7 days, such as within 1-2 days, within 2-4 days or within 5-7 days, whether there is an improvement of the clinical symptoms of the infection. In particular embodiments, in view of the efficacy of the treatment, the methods comprise determining whether there is an improvement within 1-4 or even 1-2 days.

In a further aspect, the present invention provides methods for preparing a soluble and stable formulation of A-5021 of at least 1 mg/mL. Indeed, as detailed above, the present inventors have identified ways to obtain stable solutions of increased concentration of this active ingredient, which are compatible with direct administration to the eye and/or to wounded tissue. More particularly, the compositions of the present invention are stable in that they do not precipitate, allowing repeated usage of the same batch over a period of several days up to several weeks.

More particularly, the methods of the present invention comprise the steps of:
a) providing a solution comprising at least 10% w/v of a cyclodextrin, for example hydroxypropyl beta-cyclodextrin;
b) adding A-5021 to said solution;
c) solubilizing the A-5021 added in step b);
d) repeating steps b) and c) until a concentration of A-5021 in said solution of at least 1 mg/mL is obtained;
e) optionally, adding at least 0.08 mg/mL thiomersal.

In particular embodiments, the solution provided in step a) is an aqueous solution. It will be understood that repeating steps (b) and (c) is only necessary if the concentration of 1 mg/mL has not yet been attained after the first performing of steps (b) and (c). In particular embodiments, the A-5021 is added in multiple steps, such as in 2-5 steps.

The step of solubilizing the A-5021 is typically ensured by mixing, such as by using a vortex. In particular embodiments, step c) comprises heating of the mixture obtained in step b), preferably to a temperature between 45 and 60° C. It will be understood by the skilled person however that this step may occur without requiring any particular action, especially when limited amounts of the active ingredient are added.

As indicated above, it has been found by the present inventors that the use of cyclodextrin does not require the use of solubilizing agents with an elevated pH. Thus, in particular embodiments, the methods of the invention do not comprise the addition of a solvent having a pH over 7.9.

The following non-limiting examples illustrate the present invention.

EXAMPLES

The following examples are provided for the purpose of illustrating the present invention and by no means are meant and in no way should be interpreted to limit the scope of the present invention.

a) Solubilization of A-5021 to Pharmacologically Active Concentrations

Example a1

Solubilization Tests

In order to determine the solubility of A-5021 (i.e. 2-amino-9-[[(1S,2R)-1,2-bis(hydroxymethyl)cyclopropyl]methyl]-1,9-dihydro-6H-Purin-6-one), a first series of 33 slurry experiments was performed. Within these experiments a set of 33 different systems (varying in i.e. buffers, co-solvents, solubilizing agents) were considered. The following six buffers were used: HCl buffer (pH 2), phosphate buffer (pH 6.8 and 7.4), tris(hydroxymethyl)aminoethane buffer (pH 9), sodium carbonate/bicarbonate (pH 10.8), and potassium dihydrogen phosphate (pH 12). As co-solvents dimethyl sulfoxide (DMSO), dimethyl acetamide (DMA), N-methyl pyrrolidone (NMP), ethanol (EtOH), and propylene glycol were used with varying concentrations. The solubilizing agents used were propylene glycol, glycerin, solutol HS 15, polysorbate 80, beta-cyclodextrin, hydroxypropyl beta-cyclodextrin (Kleptose® HPB), cremophor EL, cremophor RH 60, polyethylene glycol (PEG) 300, PEG 400, and sulfobutylether beta-cyclodextrin (e.g. Captisol®). The solubility was determined by filtration of the slurries after 24 h equilibration time. The A-5021 concentration in the filtrates was analyzed by High-Performance Liquid Chromatography (HPLC), from which the corresponding solubility was calculated.

It was found that addition of an organic co-solvent to the pH 12 buffered solutions does not improve the solubility. However, addition of solubilizing agents such as hydroxypropyl-β-cyclodextrin, Captisol® and propylene glycol (used at up to 80% v/v, concentration) to buffer systems with a pH above 11, did improve the solubility. The highest solubility of A-5021 (8.64 mg/mL) was obtained in 80% (v/v) propylene glycol in 20% (v/v) buffer (pH 11.3).

Based on these results, a total number of 10 additional solubility determinations were carried out considering different pH values in order to follow the influence of pH on the solubility profile of A-5021. Two different buffer systems, co-solvents, and solubilizing agents were considered with focus on systems that gave the best results as reported above. The solubility was again determined by filtration of the slurries after 24 h equilibration time. The A-5021 concentration in the filtrates was analyzed by HPLC, from which the corresponding solubility was calculated. Overall, no greater solubility values than the already reported values were found. By using an acidic pH (i.e. pH 2.8) versus the previously applied pH of 11.3, the solubility at room temperature of A-5021 decreases slightly from 8.64 mg/mL to 8.5 mg/mL. A close to neutral pH buffered system (80% v/v propylene glycol and 20% v/v phosphate buffer at pH 7.4), which is of interest to develop ophthalmic solutions (allowing topical application of A-5021 to herpes virus-infected eyes) allows to solubilize A-5021 at 8.18 mg/mL. When 2-hydroxypropyl beta-cyclodextrin (HPBC) is used as a solubilizing agent instead of propylene glycol, the solubility of A-5021 decreases compared to the propylene glycol buffered systems. Using 60% v/v HCl buffer and 40% w/v HPBC, solubility of A-5021 is 6.76 mg/mL and 4.91 mg/mL at pH 2.2 and pH 7, respectively. The further decrease in solubility of A-5021 is noted when Captisol® is used as solubilizing agent (30% w/v Captisol® and 70% w/v buffer). By further increasing the amount of propylene glycol to 5.7-33.34% v/v in a system that already contains 33.33-40% w/v/v HPBC and 33.34-54.3% v/v buffer, a decrease of the solubility of A-5021 was observed (at pH 7.0-7.4 solubility of 3.28-4.05 mg/mL of A-5021 was seen).

Based on the above indicated results and in order to be able to formulate A-5021 at pharmacologically active concentrations (preferably about 0.5 mg/mL), it was considered to investigate of additional solubilizing agents and/or keeping a high amount of propylene glycol at neutral pH. In total 28 vehicle candidates were tested to solubilize A-5021 at 5 mg/mL at neutral pH: propylene glycol at concentration ranging from 20% to 80% w/v, glycofurol at concentration ranging from 5% to 50% w/v, glycerol at concentration ranging from 15% to 50% w/v, 15% w/v glycerol+15 w/v glycofurol, 25% w/v propylene glycol+25% w/v glycofurol, propylene glycol (range: 15%-60% w/v)+glycerol (range: 5%-15% w/v), 25% w/v Kleptose® HPB+25% propylene glycol, cremophor RH 40, cremophor EL, solutol HS 15, 40-50% Kleptose® HPB, miglyol 812N, liquid paraffin, polyvinylpyrrolidone K12.

Only four vehicles allowed solubilizing A-5021 at the concentration of 5 mg/mL (0.5% w/v) at close to neutral pH (the pH ranged from 6.98-7.11). These vehicles are (% w/v in water):

(i) 80% w/v propylene glycol;

(ii) 50% w/v Kleptose® HPB;

(iii) 60% w/v propylene glycol+15% w/v glycerol;

(iv) 60% w/v propylene glycol+10% w/v glycerol.

The osmotic pressure of the propylene glycol contained formulations/solutions showed hypertonicity (high osmolality, non-physiologic). Values between 6925 mOsm and 11725 mOsm were observed, indicating the need to test local tolerance.

When tested on healthy rabbit, mouse and cat eyes local tolerance of the propylene glycol comprising solutions was good. However, when the ophthalmic solutions comprising propylene glycol were instilled to herpes virus-infected eyes of mice and cats, severe intolerance was observed. The observed clinical manifestations of local intolerance immediately post-dosing included the following: eyes closed/shut (cats and mice), vocalization (cats and mice), drooling (cats), pawing (cats), scratching eyes (cats), and shaking head (cats and mice). The severity of observations ranged from slight to severe. The observations were similar for animals treated with vehicles (i), (iii) or (iv) (the retained propylene glycol based solutions with or without glycerol not containing A-5021) and the retained propylene glycol based solutions with or without glycerol containing A-5021) indicating that the intolerance was not directly linked to the presence of A-5021, Hence, Kleptose® HPB (hydroxypropyl beta-cyclodextrin) is the sole solubilizing agent suitable for the preparation of A-5021 ophthalmic solutions comprising between 0.1% and 1% w/v A-5021, for example 0.2% to 0.5% w/v. The pH of Kleptose® HPB solution containing 0.2% to 0.5% w/v ranges from 6.0-8.0 with an osmotic pressure of about 350 mOsm.

As a multi-use solution for ophthalmic application to herpes-diseased eyes, the formulation on Kleptose® HPB has to be tested for efficacy of antimicrobial preservation. To this end, a series of nine Kleptose® HPB based formulations were tested with different antimicrobial preservatives:

no preservative;

0.01% benzalkonium chloride (BAK);

0.02% BAK;

0.01% BAK+0.01% ethylenediaminetetraacetic acid (EDTA);

0.008% Thiomersal 0.01% Thiomersal;

0.02% Thiomersal;

1.5% benzyl alcohol;

0.15% methyl para-hydroxybenzoate (PHBM)+0.05% propyl para-hydroxybenzoate (PHBP).

Preservative efficacy tests were carried out (criteria of efficacy based on those of the European Pharmacopoeia). The formulations were challenged with S. aureus, P. aeruginosa, C. albicans, A. brasiliensis (i.e. yeast, mold and bacteria) and tested at different times points post challenge (6 hours, 24 hours, 7 days, 14 days and 28 days). The Kleptose® HPB-based formulation of A-5021 without preservative did not comply with the criteria A or B of the European Pharmacopoeia justifying the inclusion of an antimicrobial preservative. The Kleptose® HPB-based formulations of A-5021 with 0.01%-0.02% BAK or 1.5% benzyl alcohol or 0.15% PHBM+0.05% PHBP did not comply with the criteria A or B. The Kleptose® HPB-based formulation of A-5021 with 0.01% BAK+0.01% EDTA did not comply with the criteria A or B. Hence, of the nine formulations tested, only the three formulations comprising thiomersal (at 0.008% w/v, 0.01% w/v and 0.02% w/v) were found sufficiently effective for Kleptose® HPB based solutions of A-5021 (at 0.2% and 0.5% w/v). The high concentration of Kleptose® HPB (i.e. hydroxyl-propyl-beta-cyclodextrin) may be responsible for the inhibition of the other preservatives.

In conclusion, the following formulations of A-5021 are retained since these formulations are compatible with the topical ocular instillation as an ophthalmic product for the treatment of herpes-related eye disease in companion animals: 0.2-0.5% w/v of A-5021 in 20%-50% w/v Kleptose® HPB using 0.008% to 0.02% w/v thiomersal as antimicrobial preservative (fill to volume with water).

Example a2

0.5% w/v A-5021 Formulation (Formulation A)

A total of 5 mg/mL of A-5021 was solubilized in a 50% w/v Kleptose® HPB solution in water, following agitation and heating to a temperature between 45 and 60° C. Afterwards, no crystallization was observed several days following storage at room temperature and storage between 2° C. and 8° C. The formulation has an osmotic pressure of 350 mOsm and a pH of 7.03.

Thiomersal was added at a concentration of 0.01% w/v as a preservative. A preservative efficacy test was conducted according to the European Pharmacopoeia general method. Sampling was performed 6 hours, 7 days, 14 days and 28 days after challenge. A 3.2 $\log_{10}$ reduction in S. aureus content and a 1.5 $\log_{10}$ reduction in P. aeruginosa content were noted 6 hours following challenge. No S. aureus and P. aeruginosa was recovered thereafter. No C. albicans or A. brasiliensis was recovered at any of the sampling points (7 days, 14 days and 28 days post challenge).

The stability of the composition comprising 0.5% w/v A-5021 and 0.01% w/v Thiomersal in 50% w/v Kleptose® HPB was assessed via an accelerated stability test, in which the composition was stored 3 months at 40° C. with 75% relative humidity. No decrease with regard to theoretical A-5021 content was noted. No appearance of degradation products over the 0.3% reporting threshold was observed. The Thiomersal content was considered as acceptable with regard to analytical and manufacturing process variations.

Example a3

0.2% w/v A-5021 Formulation (Formulation B)

A total of 2 mg/mL of A-5021 was solubilized in 20% w/v Kleptose® HPB (filled to volume with water) following agitation and heating to a temperature between 45 and 55° C. Thiomersal was added at a concentration of 0.01% w/v. The formulation had a pH of 6.4. A preservative efficacy test conducted according to the European Pharmacopoeia general method. A 2.1 $\log_{10}$ reduction in S. aureus content was noted 6 hours following challenge. No S. aureus was recovered thereafter (last sampling was done at 7 days post challenge). A 1.7 $\log_{10}$ reduction in P. aeruginosa content was noted 6 hours following challenge. No P. aeruginosa was recovered thereafter (last sampling was done at 7 days post challenge). No C. albicans or A. brasiliensis was recovered at 7 days, 14 days and 28 days post challenge. The preservative efficacy test was stopped at 7 days post challenge, since therapeutic efficacy of the composition was demonstrated already at 7 days.

The stability of the 0.2% w/v A-5021 solution in 20% w/v Kleptose® HPB and 0.01% w/v Thiomersal was assessed via an accelerated stability test, in which the composition was stored for 1 month at 40° C. with 75% relative humidity. No decrease with regard to theoretical A-5021 content was noted. No appearance of degradation products over the 0.3% reporting threshold was observed.

b) Treatment of Herpetic Infections

The ophthalmic solutions of formulation A and B as described hereabove were used for the treatment of various cats with clinical signs induced by an acute FHV-1 infection.

Example b1

Three Times Daily Treatment With 0.5% w/v A-5021 Formulation

A Chartreux male cat of 15 years old with a history of FHV-1 ocular disease (recurrency) was presented to the veterinary ophthalmologist following a new phase of acute herpetic infection. The right eye was affected and different dendritic ulcers were seen (using fluorescein staining and cobalt-blue light visualization). The cat was treated three times daily with the composition of formulation A as described above. After 10 days of treatment, the eye cat was again presented to the veterinary ophthalmologist. The right eye was completely open. Although the fluorescein test showed two small remaining epithelial branches, the ulcers were almost completely healed. Moreover, the treatment was extremely well supported, as the treatment did not cause pain, discomfort or irritation. Treatment was continued for 10 days, after which the cat was completely healed.

Example b2

Three Times Daily Treatment With 0.2% w/v A-5021 Formulation

A litter of two 5-week old European short-hair kittens (one female and one male kitten) was affected by FHV-1. FHV-1 is a typical disease in neonatal kittens leading to respiratory disease, fever, sneezing or coughing, nasal discharge and often symblepharon (i.e. partial or complete adhesion of the palpebral conjunctiva of the eyelid to the bulbar conjunctiva of the eyeball). When neonatal, the entire litter of kittens is affected to some extent.

The two kittens were presented to the veterinary ophthalmologist and were confirmed PCR (polymerase chain reaction) positive for FHV-1 on conjunctival swab samples. The left eye of the male kitten was showing signs of FHV-1 induced spectacular conjunctivitis. A dendritic ulcer was also suspected, but hard to confirm due to the swelling of the conjunctivae.

The female kitten was even more seriously affected, and had corneal edema on the left eye and a severe symblepharon on the right eye, with the third eyelid covering the entire right eye. Both kittens were treated three times daily with ophthalmic solution of formulation B as described above. After seven days of ocular instillations, the male kitten was completely healed and the female kitten was no longer infectious as demonstrated by the negative PCR results for FHV-1 (conjunctival swab samples).

Example b3

Twice Daily Treatment With 0.2% w/v A-5021 Formulation

A 6-week old male European short-hair kitten was presented to the veterinary ophthalmologist with respiratory symptoms. The left eye was kept closed and corneal edema was present, as well as little blood vessels which formed a little cornea granuloma. The kitten was diagnosed with herpes virus infection. The kitten was treated twice daily with the ophthalmic formulation B as described above, and its condition improved within 7 days of treatment: the left eye was more open, the corneal granuloma decreased and the blood vessels retracted. Some residual edema was left. Treatment was continued at the same twice daily treatment frequency, until the kitten was completely healed.

c) Diagnosis and Treatment of Herpetic Infections

Example c1

A 1-year old male European short-hair cat was presented to the veterinary ophthalmologist with the following clinical signs: sneezing and severe conjunctivitis of the right eye. The cat was diagnosed with interstitial keratitis. No corneal or dendritic ulcers were observed, therefore no definite FHV-1 clinical diagnosis could be made. Nevertheless, FHV-1 was presumed to be at origin and conjunctival swab samples are taken for FHV-1 PCR analysis. The cat tested negative for FHV-1 PCR. Hence, no FHV-1 virological diagnosis could be made. Treatment with the ophthalmic formulation A as described above was initiated; no other treatment or corticosteroids were co-administered. Marked improvement was seen in the first week of treatment. Following two weeks of treatment, the cornea was clearly visible as well as the anterior chamber of the eye. The inflammatory reaction seen at the original consult was in regression. Hence, a diagnosis of FHV-1 disease could be based on the successful treatment with A-5021 ophthalmic solution with marked improvement within the first week of treatment. This was confirmed by the continued successful treatment and clinical improvement noted 16 days post initiation of treatment. 103 days post treatment the cat was examined again, and the cornea was found to be calm and not showing any sequellae.

Example c2

A 4-year old female European short-hair cat was presented to the veterinary ophthalmologist with the following clinical signs: right eye shut with presence of multiple interstitial corneal vessels. The cat was diagnosed with interstitial keratitis having a principally vascular reaction. However, no corneal or dendritic ulcers were seen in this adult cat, therefore no definite FHV-1 clinical diagnosis could be made. Conjunctival swab samples were taken for FHV-1 PCR analysis. The cat tested negative for FHV-1 PCR. Hence, no FHV-1 virological diagnosis could be made. Tentative treatment with the ophthalmic formulation A as described above was started; no other treatment or corticosteroids were co-administered. Marked improvement was seen in the first week of treatment. Following three weeks of treatment, the cat was doing significantly better, the eye was much clearer and the corneal vessels had seriously regressed. Hence, a diagnosis of FHV-1 disease was based on the successful treatment with A-5021 ophthalmic solution with marked improvement within the first week of treatment. The diagnosis was confirmed by the continued successful treatment and clinical improvement noted 21 days post initiation of treatment.

Example c3

A total of 20 field cats of different breeds and ages, with a variety of ocular manifestations for which FHV-1 was assumed to be the underlying cause (as per the opinion of a Diplomate of the European College of Veterinary Ophthalmology), were sampled (ocular swab samples were taken for FHV-1 PCR analysis) and treated with different formulations of A-5021 (at concentration of 0.2% and 0.5%). Treatment was given topically as eye-drop instillations in the affected eyes at a frequency of 2 or 3 times per day. FHV-1 positive PCR results were obtained in 60% of these cases (12 out of 20 cats), FHV-1 negative results were obtained in 25% of the cases and for 15% of the cases no PCR results were available (due to e.g. DNA extraction failure). Of the FHV-1 PCR negative cases, all cats rapidly responded to treatment with significant clinical improvement already observed in the first week of treatment (false negatives based on PCR). In contrast, one cat found to be PCR positive for FHV-1 DNA did not respond to treatment (false positive based on PCR and on clinical diagnosis).

Hence, the specific anti-herpes drug A-5021 formulated as ophthalmic product and is a rapid diagnostic therapeutic for herpes diseased eyes.

The invention claimed is:
1. A composition comprising:
   at least 0.1% w/v 2-amino-9-[[(1S,2R)-1,2-bis(hydroxymethyl)cyclopropyl]methyl]-1,9-dihydro-6H-Purin-6-one; and
   at least 15% w/v of a cyclodextrin.
2. The composition according to claim 1, which is an aqueous solution.
3. The composition according to claim 1, wherein said composition is an ophthalmic solution.
4. The composition according to claim 1, wherein said cyclodextrin is hydroxypropyl beta-cyclodextrin.
5. The composition according to claim 1, further comprising at least 0.008% w/v thiomersal.
6. A composition according to claim 1, for use as a diagnostic or a therapeutic composition.
7. The composition according to claim 6, for use in a method for the treatment of an ocular herpetic infection.
8. The composition according to claim 7, wherein said ocular infection is an ocular infection of a companion animal.
9. The composition according to claim 8, wherein said companion animal is a feline.
10. The composition according to claim 7, wherein said method comprises applying said composition onto the eye two or three times per day for at least seven days.
11. The composition according to claim 6, for use in a method of diagnosis of an ocular herpetic infection.
12. The composition according to claim 10, wherein said ocular infection is an ocular infection in a companion animal.
13. The composition according to claim 12, wherein said companion animal is a feline.
14. A method for preparing an ophthalmic solution, comprising the steps of:
   a) providing a solution comprising at least 10% w/v of a cyclodextrin;
   b) adding 2-amino-9-[[ (1 S,2R)-1,2-bis(hydroxymethyl) cyclopropyl]methyl]-1,9-dihydro-6H-Purin-6-one to said solution;
   c) solubilizing the 2-amino-9-[[(1S,2R)-1,2-bis(hydroxymethyl)cyclopropyl]methyl]-1,9-dihydro-6H-Purin-6-one added in step b);
   d) repeating steps b) and c) until a concentration of 2-amino-94R1 S,2R)-1,2-bis(hydroxymethyl)cyclopropyl]methyl]-1 ,9-dihydro-6H-Purin-6- one in said solution of at least 1 mg/mL is obtained;
   e) optionally, adding at least 0.008 mg/mL thiomersal.
15. The method according to claim 14, wherein said cyclodextrin is hydroxypropyl beta-cyclodextrin.

* * * * *

UNITED STATES PATENT AND TRADEMARK OFFICE
CERTIFICATE OF CORRECTION

PATENT NO. : 10,967,074 B2  
APPLICATION NO. : 14/828365  
DATED : April 6, 2021  
INVENTOR(S) : Goris et al.

Page 1 of 1

It is certified that error appears in the above-identified patent and that said Letters Patent is hereby corrected as shown below:

In the Claims

Column 16, Lines 36-37; in Claim 14, delete "2-amino-9-[[ (1 S,2R)-1,2-bis(hydroxymethyl) cyclopropyl]methyl)-1,9-dihydro-6H-Purin-6-one" and insert -- 2-amino-9-[[(1S,2R)-1,2-bis(hydroxymethyl)cyclopropyl]methyl)-1,9-dihydro-6H-Purin-6-one --, therefore.

Column 16, Lines 43-44; in Claim 14, delete "2-amino-94R1 S,2R)-1,2-bis(hydroxymethyl) cyclopropyl]methyl)-1 ,9-dihydro-6H-Purin-6- one" and insert -- 2-amino-9-[[(1S,2R)-1,2-bis(hydroxymethyl)cyclopropyl]methyl)-1,9-dihydro-6H-Purin-6-one --, therefore.

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*